United States Patent [19]

Ritter et al.

[11] Patent Number: 5,367,096

[45] Date of Patent: Nov. 22, 1994

[54] PROCESS FOR THE PREPARATION OF 2,5-DI(PHENYLAMINO)TEREPHTHALIC ACID AND DIALKYL ESTERS THEREOF IN HIGH PURITY

[75] Inventors: Eberhard Ritter, Mörfelden-Walldorf; Hans Schäfer, Bad Soden am Taunus; Thomas Vollheim, Hanau; Martin Schottler, Wiesbaden, all of Germany

[73] Assignee: Hoechst Aktiengesellschaft, Frankfurt am Main, Germany

[21] Appl. No.: 932,757

[22] Filed: Aug. 20, 1992

[30] Foreign Application Priority Data

Aug. 22, 1991 [DE] Germany ............................. 4127736

[51] Int. Cl.$^5$ ............................................. C07C 229/00
[52] U.S. Cl. ........................................ 560/48; 562/457
[58] Field of Search ............................ 560/48; 562/457

[56] References Cited

U.S. PATENT DOCUMENTS

| | | |
|---|---|---|
| 3,555,087 | 1/1971 | Grosso et al. . |
| 3,671,451 | 6/1972 | Butterfield . |
| 4,432,940 | 2/1984 | Buyalos ............................ 422/135 |
| 4,981,997 | 1/1991 | Schutze et al. . |
| 5,208,365 | 5/1993 | Fuchs et al. ......................... 560/48 |

FOREIGN PATENT DOCUMENTS

| | | |
|---|---|---|
| 0363756 | 4/1990 | European Pat. Off. . |
| 1915436 | 11/1969 | Germany . |
| 3834747 | 5/1990 | Germany . |
| 52-21499 | 10/1977 | Japan . |

OTHER PUBLICATIONS

Chemical Engineers' Handbook, 1973 Robert H. Perry/Cecil H. Chilton pp. 18-58-18-67.

Primary Examiner—José G. Dees
Assistant Examiner—Samuel Barts

[57] ABSTRACT

Process for the preparation of 2,5-di(phenylamino)-terephthalic acid and dialkyl esters thereof in high purity.

The invention relates to a process for the preparation of dialkyl 2,5-di(phenylamino)terephthalates of the formula (I)

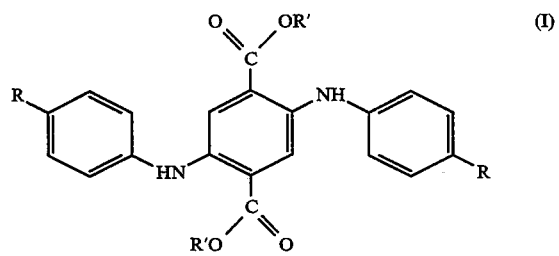

in which R is a hydrogen atom or a methyl group and R' is a methyl group or ethyl group, by dehydrogenation (oxidation) of the corresponding dialkyl 2,5-di(-phenylamino)-3,6-dihydroterephthalate with oxygen, which comprises blanketing with oxygen a solution or suspension of the dialkyl 2,5-di(phenylamino)-3,6-dihydroterephthalate in aromatic hydrocarbons in a stirred vessel, circulating this reaction mixture via a spraying device, so that the sprayed reaction mixture is distributed over the reaction mixture present in the stirred vessel, the sprayed reaction mixture being mixed with the circulating gas.

The process has the advantage of a short reaction time, combined with favorable space-time yields and simplicity in terms of apparatus.

20 Claims, 2 Drawing Sheets

PROCESS FOR THE PREPARATION OF 2,5-DI(PHENYLAMINO)TEREPHTHALIC ACID AND DIALKYL ESTERS THEREOF IN HIGH PURITY

DESCRIPTION

Process for the preparation of 2,5-di(phenyl-amino)-terephthalic acid and dialkyl esters thereof in high purity.

2,5-di(phenylamino)terephthalic acids are important intermediates for the preparation of quinacridone pigments.

The present invention relates to a technologically advantageous process for the preparation of 2,5-di(-phenylamino)terephthalic acid and dialkyl esters thereof of the formula (I)

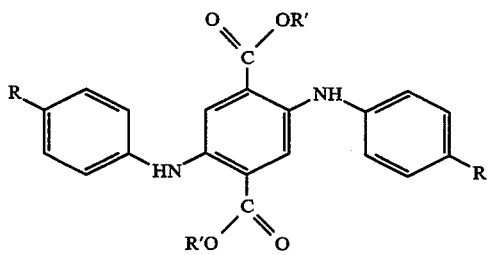

in which R is a hydrogen atom or a methyl group and R' is a hydrogen atom or a methyl or ethyl group.

It is known to prepare 2,5-di(phenylamino)terephthalic acid and dialkyl esters thereof by means of a multistep process, by cyclizing dialkyl succinates according to the manner of a Dieckmann or double Claisen condensation to give the dialkyl 2,5-dihydroxycyclohexadiene-1,4-dicarboxylate (Fortschr. chem. Forschung, Volume 1 (1950) 685–724) then transforming this into the dialkyl 2,5-di(phenylamino)-3,6-dihydroterephthalate by means of a condensation reaction with a primary phenylamine (for example aniline or toluidine) in xylene or ethylbenzene or in mixtures thereof in the presence of an aliphatic acid (for example acetic acid), dehydrogenating (oxidizing) this to give the dialkyl 2,5-di(phenylamino)terephthalate, then hydrolyzing this ester under alkaline conditions (for example in alcoholic sodium hydroxide solution) and, by treating the resulting disodium salt of 2,5-di(-phenylamino)terephthalic acid with acid, liberating the 2,5-di(phenylamino)terephthalic acid.

In the description of the preparation of di(-phenylamino)terephthalic acid by means of the route described above from succinic ester, a series of process parameters are described in the literature (JP 49-108 036; U.S. Pat. No. 35,55,087 and U.S. Pat. No. 4,981,997 (EP 0 363 756)), such as for example solvents; the intermediate isolation of individual or all synthesis step products (such as (1) dialkyl succinylsuccinate;

(2) dialkyl 2,5-di(phenylamino)-3,6-dihydroterephthalate;

(3) dialkyl 2,5-di(phenylamino)terephthalate;

(4) 2,5-di(phenylamino)terephthalic acid); the type of catalysts used, with or without additives for the abovementioned intermediates (1), (2) and (3); the time sequence of oxidation and hydrolysis (hydrolysis simultaneously with oxidation or subsequently); dehydrogenation (oxidation) agent (such as for example nitrobenzene and derivatives thereof, quinones, oxygen, iodine); work-up of the auxiliaries used (such as for example solvents, phenylamine (aniline, p-toluidine), catalysts, additives).

The invention relates to a process for the preparation of dialkyl 2,5-di(phenylamino)terephthalates of the formula (I) (see patent claim 1), in which R is a hydrogen atom or a methyl group and R' is a methyl group or ethyl group, by dehydrogenation (oxidation) of the corresponding dialkyl 2,5-di(phenylamino)-3,6-dihydroterephthalate with oxygen, which comprises blanketing with oxygen a solution or suspension of the dialkyl 2,5-di(phenylamino)-3,6-dihydroterephthalate in aromatic hydrocarbons in a stirred vessel, circulating this reaction mixture via a spraying device, so that the sprayed reaction mixture is distributed over the reaction mixture present in the stirred vessel, the sprayed reaction mixture being mixed with the circulating gas.

The starting material, dialkyl 2,5-di(phenylamino)-3,6-dihydroterephthalate, can be prepared by conventional processes. The further processing of the product to give the disodium salt and, if required, to give the corresponding acid can also be advantageously carried out in accordance with this application.

The present invention therefore further relates to a process for the preparation of 2,5-di(phenylamino)-terephthalic acid and dialkyl esters thereof of the formula (I) (see patent claim 2), in which R is a hydrogen atom or a methyl group and R' is a hydrogen atom or a methyl group or ethyl group, by (1) reacting di($C_1$–$C_2$)alkyl succinate with sodium alcoholate in xylene in the manner of a Dieckmann condensation to give the disodium salt of the di($C_1$–$C_2$)alkyl ester of 2,5-dihydroxycyclohexadiene-1,4-dicarboxylate, (2) reacting the condensation product thus obtained, after decomposition of the disodium salt by means of acid, with a phenylamine of the formula (II) (see patent claim 2), in which R has the abovementioned meaning, in the presence of an organic acid in aromatic hydrocarbons to give the di($C_1$–$C_2$)alkyl 2,5-di(phenylamino)-3,6-dihydroterephthalate, (3) dehydrogenating (oxidizing) the cyclo-1,4-hexadiene derivative thus obtained with oxygen to give the corresponding di($C_1$–$C_2$)alkyl 2,5-di(-phenylamino)terephthalate, (4) hydrolyzing the dialkyl ester thus obtained in methanolic sodium hydroxide solution to give the corresponding disodium salt of 2,5-di(phenylaanino)terephthalic acid and (5) liberating the 2,5-di(phenylamino)terephthalic acid from the said disodium salt using acid, which comprises carrying out the oxidation in stage (3) in such a manner that the reaction mixture of stage (2) present as solution or suspension is blanketed with oxygen in a stirred vessel, this reaction mixture is circulated via a spraying device, so that the sprayed reaction mixture is distributed over the reaction mixture present in the stirred vessel, the sprayed reaction mixture being mixed with the circulating gas.

The oxygen can be used alone or in a mixture with inert gases, for example in the form of air. Suitable aromatic solvents are in particular the various xylene isomers and, quite generally, those in which oxygen is as readily soluble as it is in xylene. These solvents should generally form a azeotrope with water, where the azeotropic mixture should boil at below about 120° C. For example toluene, chlorobenzene, ethylbenzene, diisopropylnaphthalene and trialkylbenzenes are thus suitable. Particular preference is given to xylene alone or industrial xylene mixtures.

For the reaction with the phenylamine of the formula (II) in stage (2), propionic acid or hexafluoropropanesulfonic acid can, for example, be used as the acid catalyst.

The circulating gas is generally a mixture of, on the one hand, the gas mixture established in dynamic equilibrium above the reaction mixture present with, on the other hand, oxygen, with or without admixed inert gases, with which mixture the reaction mixture is blanketed and which is replenished as required.

The time in which the reaction mixture is circulated once is generally 0.5 to 10 min, in particular 1 to 6 min.

The process according to the invention is expediently carried out at a temperature of the reaction mixture of from 80° to 120° C., preferably from 90° to 110° C., in particular from 95° to 100° C. At pressures higher than atmospheric pressure, higher temperatures can also be used.

The spraying device is generally a device which contains openings in the form of for example holes, slots or channels, through which the liquid to be distributed is forced. In this case, it can be in particular perforated plates or a device containing one or more nozzles, such as a device containing solid cone nozzles, ring nozzles or ejector nozzles. Ejector nozzles are self-priming nozzles, whose advantage is that the desired flow velocity of the circulating gas is produced by the suction effect of the nozzle, so that it can be transported without an additional gas compressor. In the case of other nozzles, the flow velocity in each case can be produced by means of a compressor, for example a pump which transports the circulating gas.

The reactor volume and the quantity of reaction mixture introduced, the rate at which the reaction mixture is circulated and the type, number and dimension of the spraying nozzles of the spraying device are expediently chosen so that the specific interfacial area is 200 to 7000 $m^2/m^3$, preferably 300 to 6000 $m^2/m^3$, particularly preferably 400 to 5000 $m^2/m^3$, relative to the reactor volume. The interfacial area can be influenced in particular by the size and number density of the sprayed droplets.

An advantage of the process according to the invention is the relatively short reaction time, combined with favorable space-time yields and simplicity in terms of apparatus. This is based, inter alia, on the fact that spraying the reaction mixture in the circulating gas ensures a relatively high content of dissolved oxygen in the reaction solution, so that the use of additional catalysts can be avoided, which is a particular advantage. However, catalysts of $V_4A$ steel and/or a transition metal of the Periodic Table of the Elements and/or of a rare earth metal having variable oxidation states or compounds thereof can also be used.

The acceleration of the reaction, in addition to being due to the creation of a large liquid/gas interfacial area, is also due to the reduction of the diffusion boundary layer thickness at the solid particles of the suspended starting compound, as a result of the shear forces occurring during the spraying process. The resistance to matter transport is thus reduced and the matter exchange surface enlarged.

Since the reaction time is also dependent on the partial pressure of oxygen of the circulating gas, the reaction time can be controlled in this manner, so that optimal timings can be maintained. The reaction time can be adjusted in broad ranges. Generally, reaction times of 3 to 16 hours are maintained.

The partial pressure of oxygen can also be controlled via a change of the total pressure of the gas phase in the reactor. The total pressure is generally between 1 and 10 bar, in particular atmospheric pressure.

The increased reaction rate is particularly advantageous as by this means optimal timings for the individual further processing in the conversion from stage (2) to (3) and further to stage (4) are achieved.

The process according to the invention is described in an exemplary manner with reference to FIGS. 1 and 2:

Figure 1:
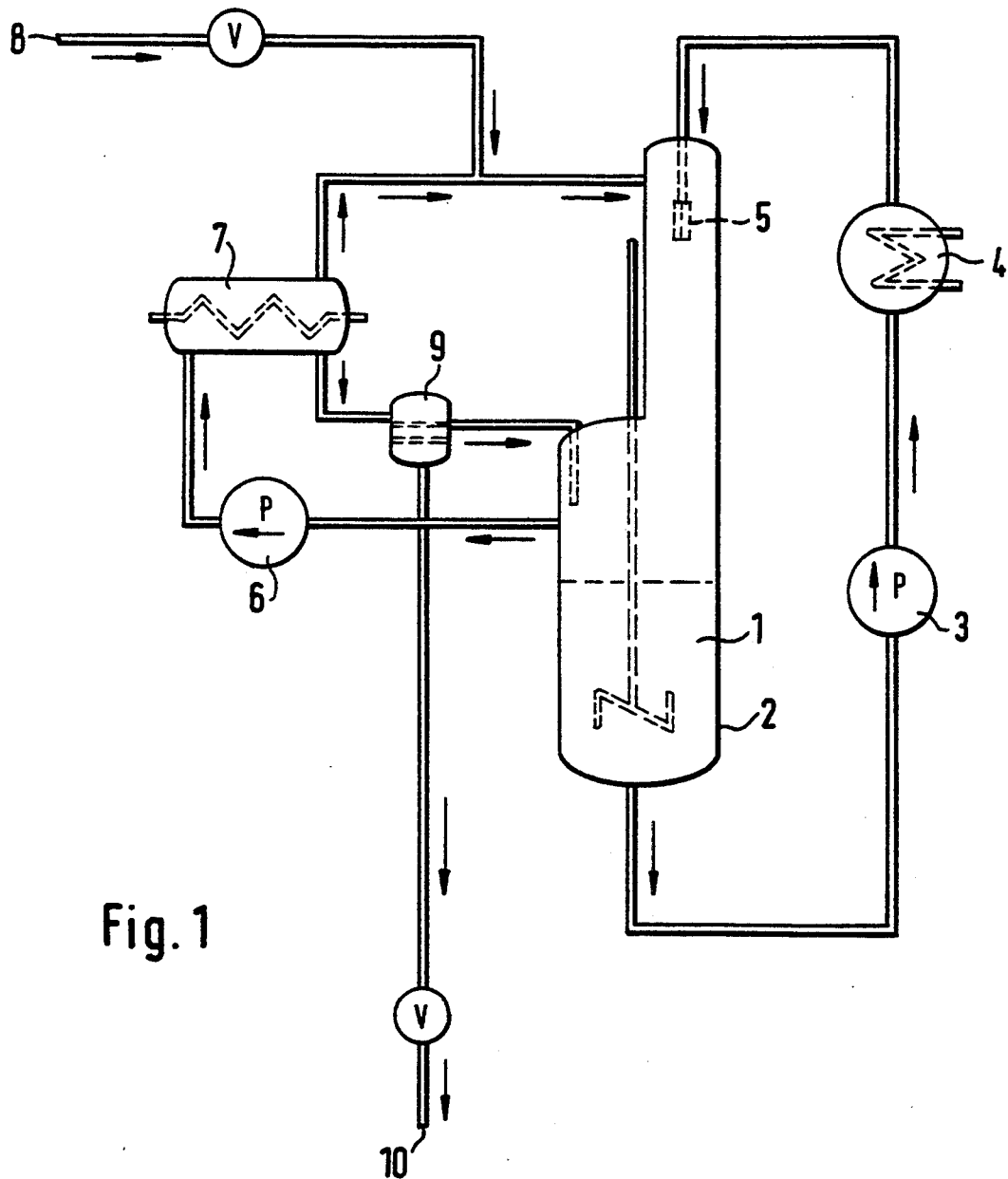
FIG. 1
Figure 2:
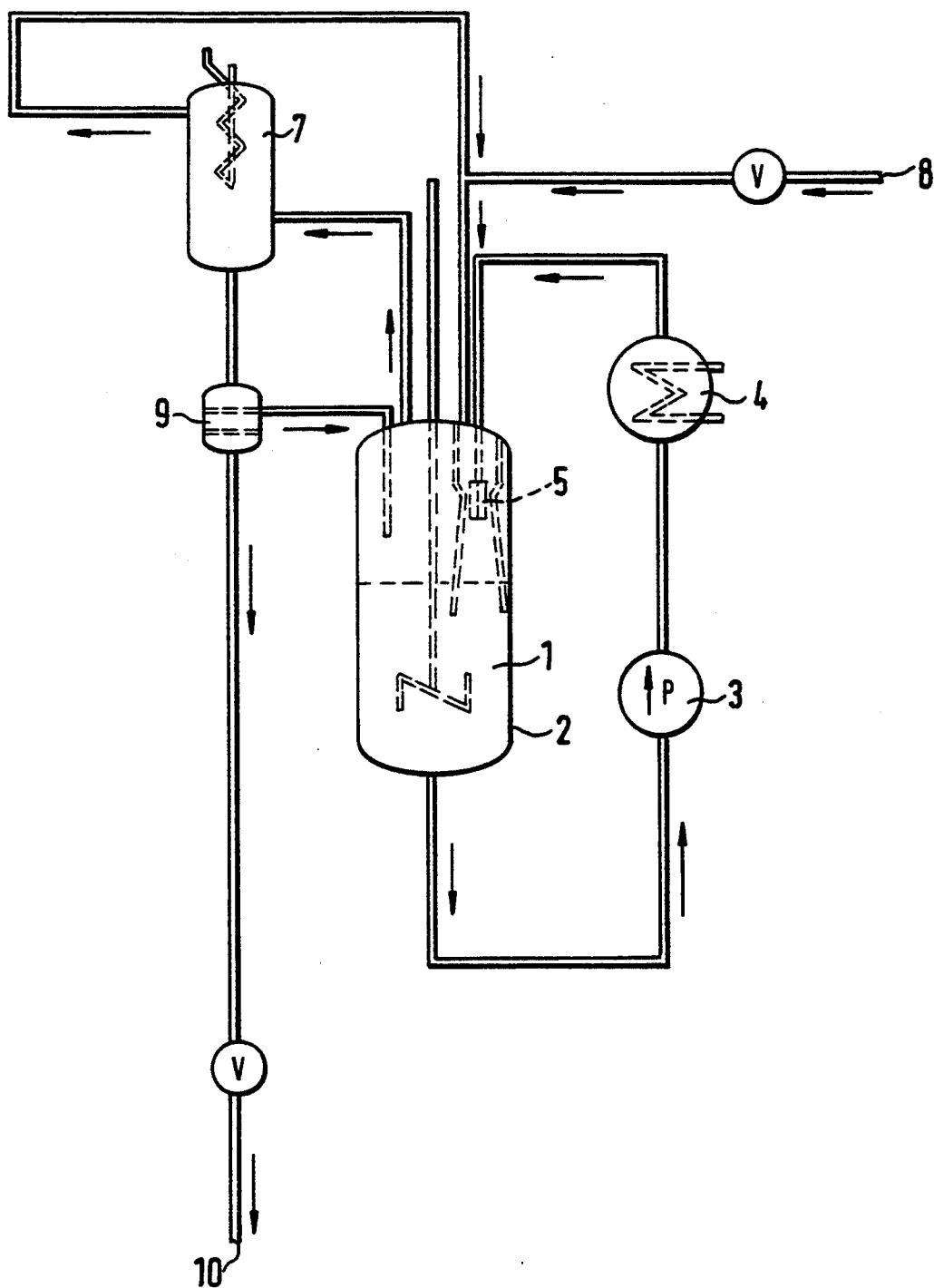

The reaction mixture 1 is introduced into a stirred container 2 and withdrawn through the base outlet and transported from the pump 3 through the heat exchanger 4 to the nozzle 5, and sprayed there. The spraying nozzle is installed in a tower-like construction mounted on the reactor. The sprayed liquid runs back into the stirred container 2. The circulated gas is withdrawn from the gas space over the reaction mixture by means of a pump 6 and is transported via the condenser 7 back into the reactor 2, a replenishment 8 of oxygen, and possibly inert gas, being appropriate to supplement the oxygen consumed. The vapor mixture condensed in the condenser 7 is passed into a phase separator 9, from which the light phase flows back into the reactor 2, and the heavy (aqueous) phase is discharged from the apparatus.

FIG. 2

The circuit for the reaction mixture is built up in an identical manner as in FIG. 1. However, the nozzle 5 is located within the vessel 2 serving as the receiver and is self-priming, so that no transport pump for the gas is required in the gas circuit. Otherwise, the gas circuit is also identically constructed, and contains a replenishing device 8 for oxygen and a discharge 10 for the water formed in the reaction.

EXAMPLES

1. A suspension of dimethyl 2,5-diphenylamino-3,6-dihydroterephthalate in xylene was introduced into a stirred vessel of 5 l volume serving as a receiver. The suspension contained 736 g of the dihydroester, 360 g of propionic acid, 72 g of aniline and 1850 g of xylene. Propionic acid and aniline originated from the preceding reaction steps. The suspension was pumped via a heat exchanger and sprayed via a solid cone nozzle having a spraying angle of 15° into a cylindrical tube. The sprayed liquid was returned to the receiver. The rate at which the liquid was circulated was 180 l/h; the diameter of the nozzle orifice was 1.6 mm. The interfacial area, relative to the reactor volume, was 400 $m^2/m^3$. After a temperature of 97° C. was attained, the circulating gas was turned on. The gas flow was 110 l/h. For the oxidation, air was used which was passed over a cooler for removal of water resulting in the reaction. The condensate (water/xylene) was separated in a phase separator, the water was ejected and the xylene was returned into the reactor. The reaction was completed after 4.5 hours; the yield of product was 99% (HPLC analysis as area percent).

2. The procedure of Example 1 was followed, but starting from a suspension of dimethyl 2,5-di(p-toluidino)-3,6-dihydroterephthalate. The suspension contained 812 g of the dihydroester, 360 g of propionic acid, 43 g of p-toluidine and 1850 g of xylene. The reaction was completed after 6.5 hours; the yield of product was 99%.

3. Example 1 was repeated, but instead of air a nitrogen/oxygen mixture containing 40% by volume of oxygen was used. The reaction was completed after 3.5 hours; the yield of product was 97%.

4. A suspension of dimethyl 2,5-di(p-toluidino)-3,6-dihydroterephthalate in xylene was introduced into a stirred vessel of 370 l volume serving as a receiver. The suspension contained 65 kg of the dihydroester, 26 kg of propionic acid, 6.5 kg of p-toluidine and 250 kg of xylene. Propionic acid and p-toluidine originated from the preceding reaction steps.

The suspension was pumped via a heat exchanger and sprayed via a solid cone nozzle having a spraying angle of 15° into a cylindrical tube. The sprayed liquid was returned to the receiver. The rate at which the liquid was circulated was 8000 l/h, the diameter of the nozzle orifice was 12 mm. The interfacial area, relative to the reactor volume, was 2800 $m^2/m^3$.

After a temperature of 97° C. was attained, the gas flow was turned on. The gas flow was 15000 l/h. For the oxidation, a nitrogen/oxygen mixture containing 8% by volume of oxygen was used. The reaction was completed after 13 h; the yield of product was 99% (HPLC analysis as area percent).

I claim:

1. A process for preparing a dialkyl 2,5-di(-phenylamino)terephthalate and optionally hydrolyzing said dialkyl 2,5-di(phenylamino)terephthalate to the corresponding 2,5-di(phenylamino)terephthalic acid, said 2,5-di(phenylamino)terephthalate having the formula (I)

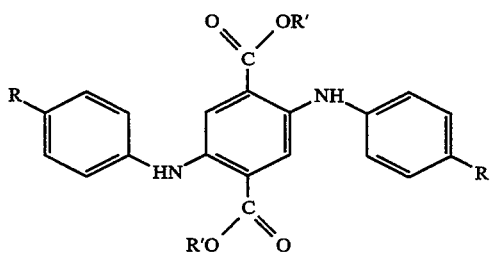

in which R is a hydrogen atom or a methyl group and R' is a methyl group or ethyl group, or, in the case of the optional hydrolysis to the corresponding 2,5-di(-phenylamino)terephthalic acid, R' is a hydrogen atom, by dehydrogenation (oxidation) of the corresponding dialkyl 2,5-di(phenylamino)-3,6-dihydroterephthalate with oxygen, which comprises blanksting with an oxygen-containing gas a solution or suspension of the dialkyl 2,5-di(phenylamino)-3,6-dihydroterephthalate in aromatic hydrocarbons in a stirred vessel, circulating this reaction mixture via a spraying device, so that the sprayed reaction mixture is distributed over the reaction mixture present in the stirred vessel, and circulating said gas, the sprayed reaction mixture being mixed with the circulating gas, and optionally hydrolyzing the resulting dialkyl 2,5-di(phenylamino)terephthalate.

2. A process as claimed in claim 1 for the preparation of the dialkyl ester of said formula (I) of claim 1 or the corresponding 2,5-di(phenylamino)terephthalic acid, wherein:

the 2,5-di (phenylamino)-3,6-dihydroterephthalate starting material of claim 1 has been obtained by (1) reacting di($C_1$–$C_2$)alkyl succinate with sodium alcoholate in xylene in the manner of a Dieckmann condensation to give the disodium salt of the di($C_1$–$C_2$)alkyl ester of 2,5-dihydrocyclohexadiene-1,4-dicarboxylate, (2) reacting the condensation product thus obtained, after decomposition of the disodium salt by means of acid, with a phenylamine of the formula (II)

in which R has the above-mentioned meaning, in the presence of an organic acid in aromatic hydrocarbons to give di($C_1$–$C_2$)alkyl 2,5-di(pheylamino)-3,6-dihydroterephthalate, and wherein:

after the said dehydrogenation has been completed, the dialkyl ester of said formula (I) is recovered as such, or the following additional steps are carried out:

hydrolyzing the dialkyl ester obtained from the said dehydrogenation in methanolic sodium hydroxide solution to give the corresponding disodium salt of 2,5-di(phenylamino) terephthalic acid, and liberating the 2,5-di(phenylamino)terephthalic acid from the said disodium salt using acid.

3. The process as claimed in claim 1 or 2, wherein the oxygen-containing gas is air.

4. The process as claimed in claim 1 or 2, wherein the time in which the reaction mixture is circulated once is 0.5 to 10 min.

5. The process as claimed in claim 1 or 2, wherein the reaction is carried out at temperatures of from 80° to 120° C.

6. The process as claimed in claim 1 or 2, wherein the specific interfacial area is 200 to 7000 $m^2/m^3$, relative to the reactor volume.

7. The process as claimed in claim 1 or 2, wherein the total pressure of the gas phase in the reactor is between 1 and 10 bar.

8. The process as claimed in claim 1 or 2, wherein the time in which the reaction mixture is circulated once is 1 to 6 min.

9. The process as claimed in claim 1 or 2, wherein the reaction is carried out at temperatures from 90° to 110° C.; wherein the specific interfacial area is 300 to 6000 $m^2/m^3$, relative to the reactor volume; and wherein the total pressure of the gas phase in the reactor is at about atmospheric pressure.

10. The process as claimed in claim 1 or 2, wherein the reaction is carried out at temperatures from 95° to 100° C.; wherein the specific interfacial area is 400 to 5000 $m^2/m^3$, relative to the reactor volume; and wherein the total pressure of the gas phase in the reactor is at about atmospheric pressure.

11. The process as claimed in claim 1, wherein the spraying device contains one or more nozzles.

12. The process as claimed in claim 2, wherein the spraying device contains one or more nozzles, and the reaction mixture comprises a suspension of the dialkyl 2,5-di(phenylamino)-3,6-dihydroterephthalate.

13. The process as claimed in claim 11 or 12, wherein the nozzle is a solid cone nozzle, ring nozzle or ejector nozzle.

14. The process as claimed in claim 11 or 12, wherein the nozzle is self-priming.

15. The process as claimed in claim 2, wherein said additional steps are carried out, and said 2,5-di(phenylamino)terephthalic acid is recovered as the product of the process.

16. The process as claimed in claim 1, wherein the reaction between the dialkyl 2,5-di(phenylamino)-3,6-dihydroterephthalate and the oxygen-containing gas is carried out in the absence of a catalyst or in the presence of a catalyst consisting essentially of a transition metal of the Periodic Table of the Elements, said transition metal having a plurality of oxidation states, or a compound of said transition metal.

17. The process as claimed in claim 16, wherein the transition metal is $V_4A$ steel or a rare earth metal.

18. The process as claimed in claim 1, wherein said stirred vessel defines an essentially enclosed gas space above the reaction mixture, said spraying device being located in closely spaced relation to the upper end of said essentially enclosed gas space.

19. The process as claimed in claim 18, wherein said stirred vessel is in communication with:

liquid circulating means, external to said essentially enclosed gas space, for withdrawing reaction mixture from said vessel and circulating it to said spraying device;

gas and vapor circulation means, external to said essentially enclosed gas space, for withdrawing gas and vapor from said essentially enclosed gas space, condensing the vapor, returning gas to said gas space and condensed vapor to said vessel;

gas introduction means for introducing oxygen-containing gas into said vessel to replace the oxygen-containing gas consumed in the reaction between said gas and the dialkyl 2,5-di(phenylamino)-3,6-dihydroterephthalate; and water removal means for removing water of reaction from said vessel.

20. The process as claimed in claim 19, wherein said gas introduction means is included in said spraying device or in said gas circulation means, and said water removal means is included in said gas and vapor circulation means, the water of reaction and some aromatic hydrocarbon being removed from said vessel as water vapor and aromatic hydrocarbon vapor, said water removal means including means for separating condensed water from condensed aromatic hydrocarbon.

* * * * *